United States Patent [19]

Baldwin et al.

[11] 4,110,456
[45] Aug. 29, 1978

[54] 4-SUBSTITUTED-2-ARYLIMIDAZOLES

[75] Inventors: John J. Baldwin, Lansdale; Frederick C. Novello, Berwyn, both of Pa.

[73] Assignee: Merck & Co., Inc., Rahway, N.J.

[21] Appl. No.: 773,248

[22] Filed: Mar. 1, 1977

[51] Int. Cl.$^2$ .................... C07D 471/02; A61K 31/34
[52] U.S. Cl. .............................. 424/263; 260/294.8 F; 260/294.8 G
[58] Field of Search ................. 260/294.8 F, 294.8 G; 424/263

[56] References Cited

U.S. PATENT DOCUMENTS 3,850,944  11/1974  Tanaka et al. ................ 260/294.8 G

*Primary Examiner*—Alan L. Rotman
*Attorney, Agent, or Firm*—Michael C. Sudol, Jr.; Daniel T. Szura

[57] ABSTRACT

4-Substituted-2-arylimidazoles, wherein the 4-substituent is sulfur containing, are disclosed. The compounds have pharmaceutical activity.

4 Claims, No Drawings

4-SUBSTITUTED-2-ARYLIMIDAZOLES

BACKGROUND OF THE INVENTION

The present invention is directed to 4-sulfur containing substituted-2-arylimidazoles having antihypertensive and/or xanthine oxidase inhibiting activity.

4-Non-sulfur containing substituted 2-aryl (or alkyl) imidazoles are disclosed in U.S. Pat. No. 3,691,178, issued Sept. 12, 1972. These compounds have xanthine oxidase inhibiting activity. U.S. Pat. No. 3,786,061 discloses 4-trifluoromethyl-2-arylimidazoles having pharmaceutical activity as antihypertensives and xanthine oxidase inhibitors.

The compounds of the present invention are 2-arylimidazoles having a sulfur bearing substitutent in the 4-position — and having antihypertensive and/or xanthine oxidase inhibiting activity.

SUMMARY OF THE INVENTION

4-Sulfur containing substituted 2-arylimidazoles, their preparation and pharmaceutical use.

DESCRIPTION OF PREFERRED EMBODIMENTS

A preferred embodiment of the present invention is compounds having the formula

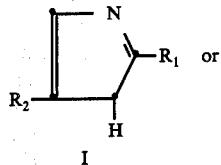

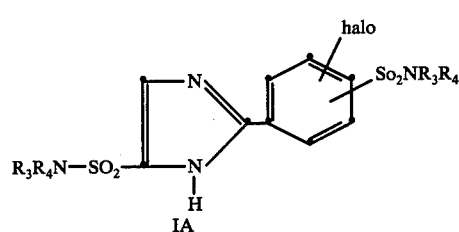

and pharmaceutically acceptable salts thereof wherein
  $R_1$ is selected from the group consisting of monohalo (e.g. Cl, Br, I or F)-phenyl, dihalo[1](e.g. Cl or Br)-phenyl and pyridyl (e.g. 3-pyridyl, 4-pyridyl),
  $R_2$ is selected from the group consisting of $C_1$-$C_5$alkyl-S-, $C_1$-$C_5$alkyl-SO-, $C_1$-$C_5$alkyl-$SO_2$- and $R_3R_4N$-$SO_2$-, and
  $R_3$ and $R_4$ are independently selected from H, $C_1$-$C_5$alkyl and hydroxy substituted $C_2$-$C_5$alkyl,
excluding compounds where $R_1$ is 4-chlorophenyl and $R_2$ is $C_1$-$C_5$alkyl-SO- or $C_1$-$C_5$alkyl-$SO_2$-.

These compounds are 2,4(5)disubstituted imidazoles.

The alkyl moiety in the $R_2$ groups defined above includes branched and straight chain alkyl groups such as $CH_3$—, t-butyl, n-pentyl and the like. The hydroxy substituted $C_2$-$C_5$ alkyl groups are also branched and straight chain alkyls having 1-2 hydroxy groups — the monohydroxy straight chain alkyls are preferred e.g. —$CH_2$-CHOH-$CH_3$ and —$(CH_2)_5$-OH.

The pharmaceutically acceptable salts include metal salts e.g. Na, K, the alkaline earth metals, quaternary salts and acid addition salts of the Formula I compounds. The metal salts can be prepared by conventional treatment of the Formula I compound with suitable base, e.g. NaOH, KOH, CaO etc. The quaternary salts can be prepared where the $R_1$ group is pyridyl by conventional treatment of the Formula I compound with an alkyl iodide such as methyl iodide, ethyl iodide and the like. The acid addition salts can be prepared by conventionally treating the Formula I compound where the $R_1$ group is pyridyl with a suitable inorganic or organic acid. Suitable inorganic acids are the hydrohalides e.g. HCl, HI, HBr, sulfuric acid, phosphoric acid and the like. Suitable organic acids are exemplified by $C_2$-$C_{24}$ carboxylic acids such as acetic acid, tetracosanic acid, oleic acid, 2-ethylhexoic acid, maleic acid, pamoic acid, lactic acid, citric acid, succinic acid, malic acid, trimethylacetic acid, oxalic acid, fumaric acid, cyclohexyl carboxylic acid, lauric acid and the like - and non-carboxylic acids such as isethionic acid.

A preferred class of compounds are those having the formula

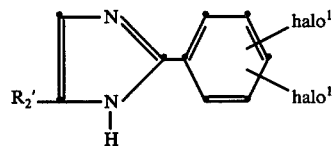

where halo[1] preferably are in the 3,4 position and are both chloro or bromo — and more preferably chloro. In a most preferred Formula II compound, halo[1] substitution is 3,4-dichloro and $R_2'$ is $H_2NSO_2$—.

A representative compound of Formula II shows xanthine oxidase inhibiting activity when tested in vitro.

Another preferred embodiment is a compound having the formula

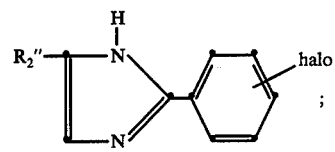

halo, in Formula III, is preferably in the 4-position, more preferably 4-bromo or 4-chloro and most preferably 4-chloro. $R_2''$ is preferably $C_1$-$C_5$alkyl-S— or $R_3R_4N$-$SO_2$— where $R_3$ and $R_4$ are independently selected from hydrogen, $C_1$-$C_5$alkyl and hydroxy-$C_2$-$C_5$ alkyl.

Compounds of Formula III exhibit random activity as xanthine oxidase (x.o.) inhibitors and antihypertensive agents. The x.o. inhibiting activity is determined in an in vitro test — the antihypertensive activity is determined by administration of the compound to a spontaneously hypertensive (SH) rat. The antihypertensive and x.o. inhibiting activities of representative Formula III compounds, where tested, are tabulated below.

TABLE I

Antihypertensive and X.O. Inhibiting Activity for Compounds of Formula

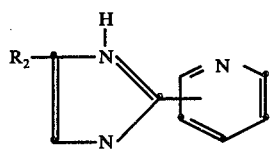

| $R_2'$ Substituent | Anti-hypertensive Activity | X.O. Inhibiting Activity |
|---|---|---|
| $(CH_3)_2CH-S-$ | yes | no |
| $H_3C-S-$ | yes | yes |
| $(H_3C)_2N-SO_2-$ | no | yes |
| $H_2N-SO_2-$ | yes | no |
| $HO-CH_2-CH_2-NH-SO_2-$ | yes | — |

Another preferred embodiment is a compound having the formula

IV

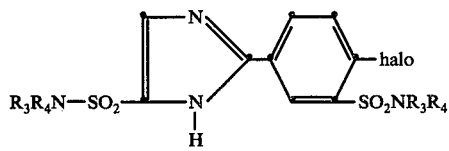

In preferred compounds of Formula IV, the pyridyl group is 3-pyridyl and $R_2$ is $R_3'R_4'N-SO_2-$ where $R_3'$ and $R_4'$ are independently selected from hydrogen and $C_1-C_5$alkyl. Compounds of Formula IV have exhibited antihypertensive activity in the SH rat. The compounds of Formula IV may also have x.o. inhibiting activity.

Another preferred embodiment is compounds having Formula IA. A more preferred embodiment is compounds having the formula

IVA wherein halo is Cl, Br, I or F and $R_3$ and $R_4$ is as defined above. Compounds of Formula IV A where halo is Cl or Br are more preferred. Hydrogen is a preferred definition of $R_3$ and $R_4$.

Compounds of Formula IA or IV A are xanthine oxidase inhibitors and/or antihypertensives.

The xanthine oxidase inhibiting activity of the present compounds indicates that they will be useful for treating gout and hyperuricemia in human patients. Administration of the compounds may be oral or parenteral, using appropriate dosage forms e.g. tablets, capsules, sterile solutions, elixirs etc. Daily dosage for this utility may be varied, ranging from about 20 mg to about 1.5 gm and preferably from about 100 to about 800 mg.

The antihypertensive activity exhibited by the present compounds indicates that they will be useful for treating hypertension (lowering blood pressure) in human patients. Administration of the compounds may be oral or parenteral e.g. intravenous, intraperitoneal, intramuscular, etc., using appropriate dosage forms, e.g. tablets, capsules, sterile solutions, emulsions etc. Daily dosage for the utility may be varied ranging from about 10 mg to about 1500 mg, preferably from about 100 mg to about 1000 mg.

The $R_3R_4N-SO_2-$ substituted compounds of Formula I are prepared by the general route illustrated by the following reactions

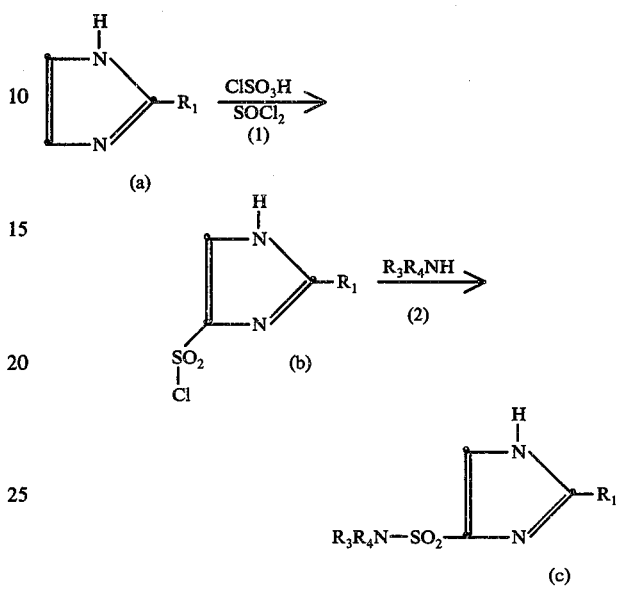

Where $R_1$ is monohalophenyl, e.g. 4-bromophenyl, 4-iodophenyl, 2-fluorophenyl, 3-chlorophenyl and the like, chlorosulfonation occurs at the 4(5) imidazole position when the chlorosulfonation is carried out at or below about 100° C. When the chloro sulfonation temperature is higher [above about 100° C to the reflux temperature of the chlorosulfonating agent $(ClSO_3H/SOCl_2)$], chlorosulfonation of the phenyl ring also occurs. Treatment of this dichlorosulfonated product with amines or ammonia yields the compounds of Formula IA, as illustrated by the following equations:

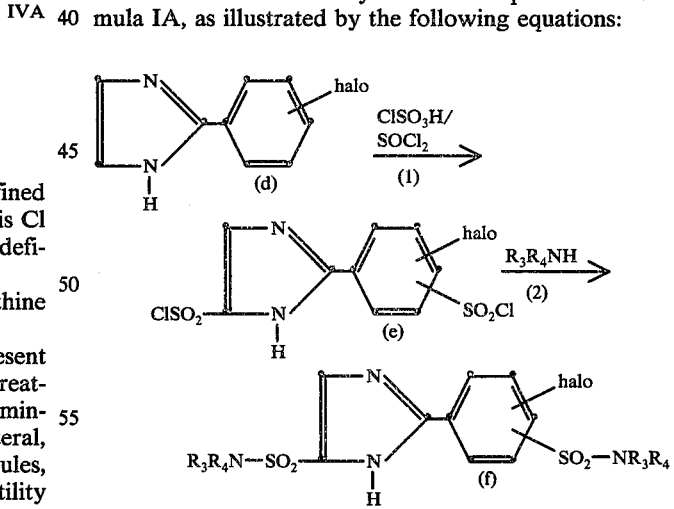

The amination reaction (2) can be carried out with excess $R_3R_4NH$ as solvent, or with a solution of $R_3R_4NH$. Solvents, such as water, ether, chloroform, methylene chloride, can be used. Amination temperatures may vary over a wide range. A convenient temperature range for primary or secondary amines or $R_3R_4NH$ solutions is 0° C to 100° C. When dichlorosulfonyl products such as (e) are employed, the $R_3$ and $R_4$ substituents present in the $R_3R_4NH$ reactant appear as substituents in both sulfamoyl groups. Compounds of formula (d) may be conveniently prepared by reacting a 1,2 diketone with ammonia and the appropriate halobenzaldehyde [Davidson et al, J. Org. Chem., 2, 319, (1937)] The chlorosulfonation (1) is carried out under conditions essentially as those described in Journal of Organic Chemistry 25, 965 (1960).

The $C_1-C_5$alkyl-S—, $C_1-C_5$alkyl-SO— and $C_1-C_5$alkyl-$SO_2$— substituted compounds of Formula I are prepared according to the procedure illustrated by the following reaction equation.

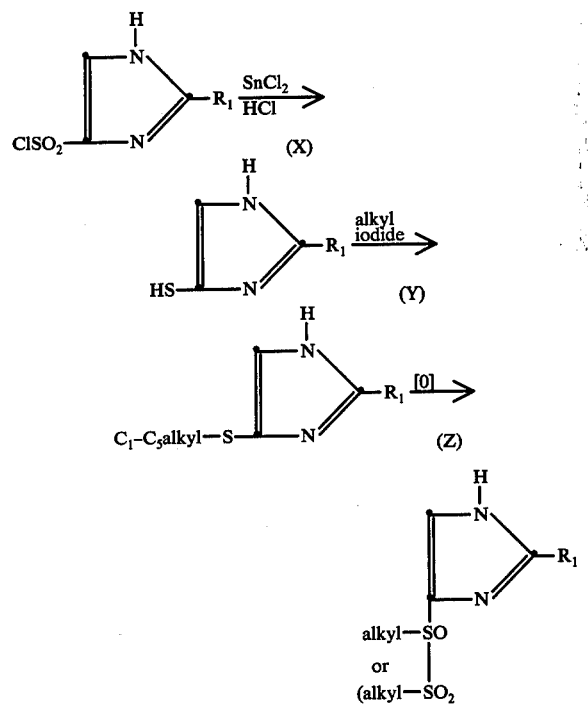

The reduction (X) was carried out according to the procedure described in Journal of Organic Chemistry 24, 289 (1959). The alkylsulfide is prepared by treating the thiol with an alkyl iodide (Y). The sulfide is oxidized (Z) to prepare the sulfinyl or sulfonyl analog.

The following examples illustrate preparation of representative intermediates and compounds of the present invention. All temperatures are in ° C unless otherwise indicated.

EXAMPLE 1

Preparation of 2-(4-chlorophenyl)-4(5)sulfamoylimidazole

A. 2-(4-chlorophenyl)imidazole (6 g., 0.034 mole) was added portionwise at room temperature with stirring to chlorosulfonic acid (30 ml.). The mixture was heated 2 hours at 100° and cooled to room temperature. Thionyl chloride (3 g.) was added and the mixture again heated for 2 hours at 100°. After cooling to room temperature the mixture was added cautiously to ice and water. A semi-solid separated and was extracted with ether. The ether layer was dried and concentrated to yield 2-(4-chlorophenyl)-4-chlorosulfonylimidazole (1.3 g., 0.005 mole).

B. 2-(4-Chlorophenyl)-4-chlorosulfonylimidazole (1 g., 0.0036 mole) was added portionwise with stirring to liquid ammonia (100 ml.). The ammonia was allowed to evaporate yielding a solid which was triturated with ether. The insoluble solid was removed by filtration and washed with water. The ether solution was concentrated to a solid and the two portions of solid were combined and recrystallized from acetonitrile to yield 0.36 g. of 2-(4-chlorophenyl)-4(5)-sulfamoylimidazole, m.p. 242°–245°.

EXAMPLE 2

Preparation of 2-(4-chlorophenyl)-4(5)-dimethylsulfamoylimidazole

To a solution of 2-(4-chlorophenyl)-4(5)-chlorosulfonyl imidazole (1.3 g., 0.005 mole) in dioxane (15 ml.) was added dropwise with stirring at room temperature a 25% aqueous solution of dimethylamine (2 g.). After 1 hour the reaction mixture was concentrated under reduced pressure (25 mm); water (10 ml.) was added and the solid filtered. After recrystallization from acetonitrile 0.55 g. of 2-(4-chlorophenyl)-4(5)-dimethylsulfamoylimidazole melting at 211°–213° was obtained.

EXAMPLE 3

Preparation of 2-(4-chlorophenyl)-4-methylsulfamoylimidazole

Substituting aqueous methylamine for the dimethylamine in Example 3 2-(4-chlorophenyl)-4-methyl-sulfamoylimidazole, melting at 246°–248°, was obtained (4.4% yield).

EXAMPLE 4

Preparation of 2-(3,4-dichlorophenyl)-4(5)-sulfamoylimidazole 2-(3,4-Dichlorophenyl)imidazole (3.0 g., 0.014 mole) was added with stirring to chlorosulfonic acid (15 ml.). The mixture was heated 2 hours at 150°, cooled to room temperature and thionyl chloride (1.5 g.) was added. the solution was heated an additional 2 hours at 150°, cooled and added cautiously to ice and water. The resulting solid was filtered, washed with water and added to liquid ammonia (25 ml.). After stirring 2 hours, the ammonia was allowed to evaporate and the residue recrystallized from acetonitrile and then from methanol-water to yield 1.5 g. of 2-(3,4-dichlorophenyl)-4(5)-sulfamoylimidazole melting at 243°–244.5°.

EXAMPLE 5

Preparation of 2-(4-chloro-3-sulfamoylphenyl)-4(5)-sulfamoylimidazole 2-(4-Chlorophenyl)imidazole (3.0 g., 0.017 mole) was added portionwise with stirring to chlorosulfonic acid (15 ml). The mixture was heated 2 hours at 110°, cooled and thionyl chloride (1.5 g.) was added. The solution was again heated at 170° for 2 hours. After cooling to room temperature, the mixture was cautiously added to ice and water. The resulting solid was filtered, washed with water and added portionwise to liquid ammonia (50 ml.). After stirring 2 hours the ammonia was allowed to evaporate and the resulting solid recrystallized from water-dimethylformamide to yield 1 g. of 2-(4-chloro-3-sulfamoylphenyl)-4(5)-sulfamoylimidazole melting, with decomposition, at 338° C.

EXAMPLE 6

Preparation of 2-(3-pyridyl)-4(5)-methylsulfamoylimidazole

A solution of chlorosulfonic acid (10 ml.) and 2-(3-pyridyl)imidazole (2.0 g., 0.014 mole), was heated at reflux for 7 hours and cooled to room temperature. Thionyl chloride (1.1 ml.) was added and the solution was heated an additional 8 hours at reflux. The excess chlorosulfonic acid was distilled off under reduced pressure (5 mm) and the residue treated with 40% aqueous methylamine (25 ml.). After standing 17 hours at room temperature, the solution was concentrated to dryness under reduced pressure (25 mm). The residue was chromatographed on alumina (Brinkmann-activity 2) and eluted with 2% methanol-chloroform to give 0.52 g. (16%) of 2-(3-pyridyl)-4(5)-methylsulfamoylimidazole melting at 212°–213° after crystallization from methanol-toluene.

Using 28–30% aqueous ammonia in place of the methylamine in the Example 6 procedure, 2-(3-pyridyl)4(5)-sulfamoylimidazole, melting at 274°–275°, was obtained (11% yield).

Replacing the aqueous methylamine in the Example 6 procedure with a 25% solution of diethylamino in dioxane, 2-(3-pyridyl)-4(5)-diethylsulfamoylimidazole, melting at 150°–152°, was obtained (9% yield).

EXAMPLE 7

Preparation of 2-(4-chlorophenyl)-4(5)-methylthioimidazole

To a solution of 2-(4-chlorophenyl)-4(5)-chlorosulfonylimidazole (1.7 g., 0.00615 mole) in acetic acid (35 ml.) was added a solution of stannous chloride dihydrate (7 g., 0.031 mole) in concentrated hydrochloric acid (6 ml.) with stirring at 65°. After heating at 65°–75° for ½ hour, the reaction mixture was cooled and poured into water (125 ml.) containing concentrated hydrochloric acid (6 ml.). A yellow solid, 2-(4-chlorophenyl)-4-mercaptoimidazole was filtered off, washed with water and suspended in water (25 ml.). To the stirred suspension under nitrogen was added a 20% aqueous solution of sodium hydroxide (5 ml.); methyl iodide (3.4 g., 0.024 mole) was then added. After stirring 1.5 hours, 2-(4-chlorophenyl)-4(5)-methylthioimidazole was removed by filtration, recrystallized from benzene and sublimed at 160° and 0.2 mm to yield 0.5 g. (58%), m.p. 170°–172°.

Using isopropyl iodide in place of the methyl iodide, and $K_2CO_3$ in dimethylformamide (DMF) in place of the aqueous sodium hydroxide in Example 7, 2-(4-chlorophenyl)-4(5-isopropylthioimidazole, melting at 195°–197°, was obtained.

EXAMPLE 8

Preparation of 2-(4-chlorophenyl)-4(5)-methylsulfinylimidazole

To 700 mg. (0.003 mole) of 2-(4-chlorophenyl)-4(5)-methylthioimidazole in acetic acid (5 ml.) was added with stirring at room temperature 30% hydrogen peroxide (5 drops). Two additional portions of 30% hydrogen peroxide (5 drops) were added after 2 and 4 hours. Two hours after the last addition of hydrogen peroxide, water (10 ml.) was added and the solution was neutralized with 10% aqueous sodium hydroxide solution. An oil separated, solidified and was filtered. After recrystallization from hexane, 500 mg. (69.2%) of 2-(4-chlorophenyl)-4(5)methylsulfinylimidazole melting at 176° C was obtained.

2-(4-Chlorophenyl)-4(5)-isopropylsulfinylimidazole, melting at 173°–175°, was obtained according to the procedure of Example 8 using 2-(4-chlorophenyl)-4(5)-isopropylthioimidazole in place of the 2-(4-chlorophenyl)-4(5)-methylthioimidazole, and carrying the reaction out for 2 hours at 100° instead of 6 hours at room temperature.

EXAMPLE 19

Prepartion of 2-(4-chlorophenyl)-4(5)-methylsulfonylimidazole

To 2-(4-chlorophenyl)-4(5)-methylthioimidazole (0.7 g., 0.003 mole) in acetic acid (7 ml.) was added at room temperature 30% hydrogen peroxide (15 drops) and the mixture heated 1.5 hours at 100°. A second portion of 30% hydrogen peroxide (15 drops) was added and heating continued for 1.5 hours. The solution was neutralized with 10% aqueous sodium hydroxide solution and 2-(4-chlorophenyl)-4(5)-methylsulfonylimidazole separated, was filtered and recrystallized from acetonitrile-water to yield 300 mg. (37.7%). melting at 210°–211°.

EXAMPLE 10

Preparation of 2-(4-chlorophenyl)-4-(2-hydroxyethylsulfamoyl)-imidazole

To a solution of 2-(4-chlorophenyl)-4-chlorosulfonylimidazole (1.3 g 0.005 m) in dioxane (15 ml) was added ethanolamine (0.61 g 0.01 ml). After 15 minutes the dioxane was removed under reduced pressure (20 mm) to yield a gum. The gum was slurried with water to yield a solid. The solid was filtered and recrystallized from acetonitrile to give 400 mg of 2-(4-chlorophenyl)-4-(2-hydroxyethylsulfamoyl)imidazole melting at 210°–212°. (20% yield). What is claimed is:

1. A compound having the formula:

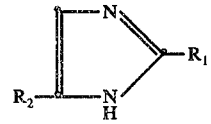

wherein $R_1$ is pyridyl, $R_2$ is selected from the group consisting of $C_1$–$C_5$alkyl-S—, $C_1$–$C_5$alkyl-SO—, $C_1$–$C_5$alkyl-$SO_2$— and $R_3R_4N$-$SO_2$—, and $R_3$ and $R_4$ are independently selected from H, $C_1$–$C_5$alkyl and hydroxy substituted $C_2$–$C_5$alkyl.

2. Compounds of claim 1 having formula I wherein $R_1$ is 3-pyridyl.

3. The compound of claim 2 wherein $R_2$ is $H_2NSO_2$—, $CH_3NH$-$SO_2$— or $(C_2H_5)_2N$-$SO_2$—.

4. An antihypertensive composition comprising an effective amount of a compound selected from the group consisting of 2-(3-pyridyl)-4-methylsulfamoylimidazole and 2-(3-pyridyl)-4(5)-diethylsulfamoylimidazole.

* * * * *